United States Patent

Godat et al.

Patent Number: 5,472,431
Date of Patent: Dec. 5, 1995

[54] INSERT DEVICE FOR FACILITATING LIMITED ASPIRATION OF A DELIVERY APPARATUS

[75] Inventors: James F. Godat, St. Louis; Max D. Adams, St. Charles, both of Mo.

[73] Assignee: Mallinckrodt Medical, Inc., St. Louis, Mo.

[21] Appl. No.: 297,883

[22] Filed: Aug. 30, 1994

Related U.S. Application Data

[62] Division of Ser. No. 988,275, Dec. 14, 1992, Pat. No. 5,370,621.

[51] Int. Cl.$^6$ ............................................ A61M 5/32
[52] U.S. Cl. ........................ 604/199; 604/187; 604/208; 604/218
[58] Field of Search .................................. 604/110, 187, 604/195, 199, 208, 213, 218, 220, 221, 228, 229

[56] References Cited

U.S. PATENT DOCUMENTS

| | | |
|---|---|---|
| 3,253,592 | 5/1966 | Von Pechmann . |
| 4,233,975 | 11/1980 | Yerman . |
| 4,246,898 | 1/1981 | Travalent et al. . |
| 4,314,556 | 2/1982 | Ma . |
| 4,317,446 | 3/1982 | Ambrosio et al. . |
| 4,365,626 | 12/1982 | House . |
| 4,390,016 | 1/1983 | Riess . |
| 4,568,336 | 2/1986 | Cooper . |
| 4,636,198 | 1/1987 | Stade . |
| 4,636,202 | 1/1987 | Lowin et al. . |
| 4,677,980 | 7/1987 | Reilly et al. . |
| 4,705,509 | 11/1987 | Stade . |
| 4,781,684 | 11/1988 | Trenner ................. 604/110 |
| 4,790,822 | 12/1988 | Haining . |
| 4,861,335 | 8/1989 | Reynolds . |
| 4,883,472 | 11/1989 | Michel . |
| 4,915,692 | 4/1990 | Verlier . |
| 4,976,693 | 12/1990 | Haast . |
| 5,135,512 | 8/1992 | Mazurik et al. . |
| 5,344,409 | 9/1994 | Ennis, II et al. ............... 604/187 |
| 5,370,621 | 12/1994 | Godat et al. ................. 604/187 |

FOREIGN PATENT DOCUMENTS 0478281  4/1992  European Pat. Off. ............... 604/110

Primary Examiner—Corrine M. Maglione
Assistant Examiner—N. Kent Gring
Attorney, Agent, or Firm—Rothwell, Figg, Ernst & Kurz

[57] ABSTRACT

A delivery apparatus in the form of a syringe assembly and piston with structure for preventing withdrawal of the piston a distance more than the thickness of one piston. The syringe is preferably prefilled and sterilized to provide a sterile syringe assembly with sterile fluid contents. Controlled, limited withdrawal of the piston facilitates aspiration of the syringe without the contamination risks caused by withdrawing the piston so as to allow the sterile fluid to contact the exposed portion of the syringe container portion behind the piston.

8 Claims, 4 Drawing Sheets

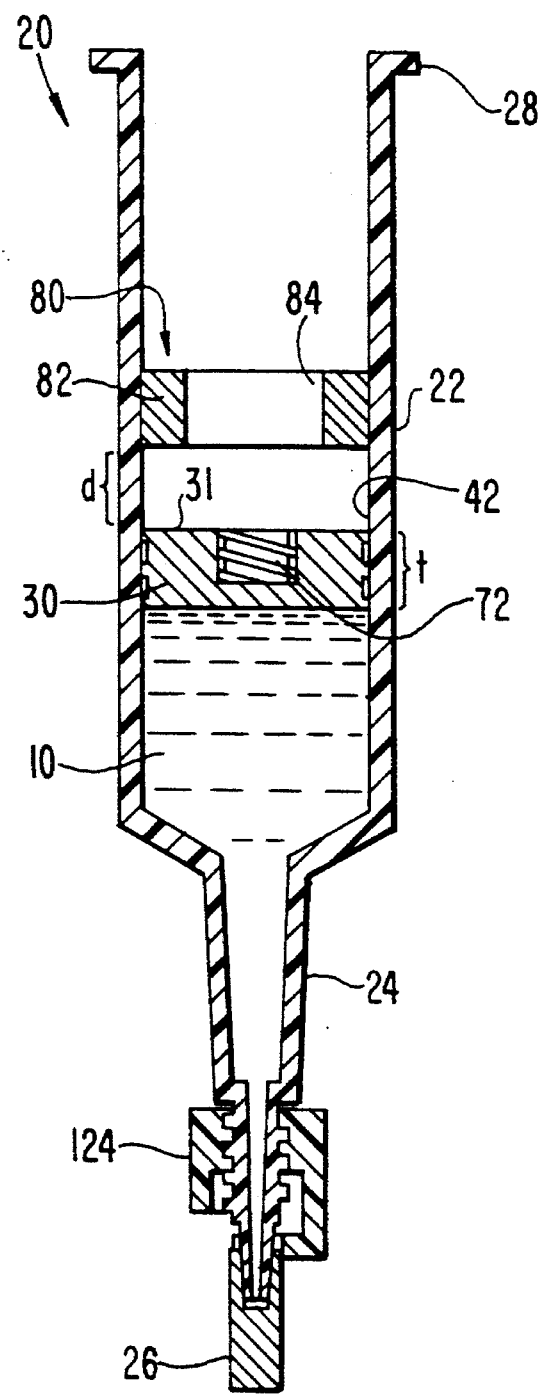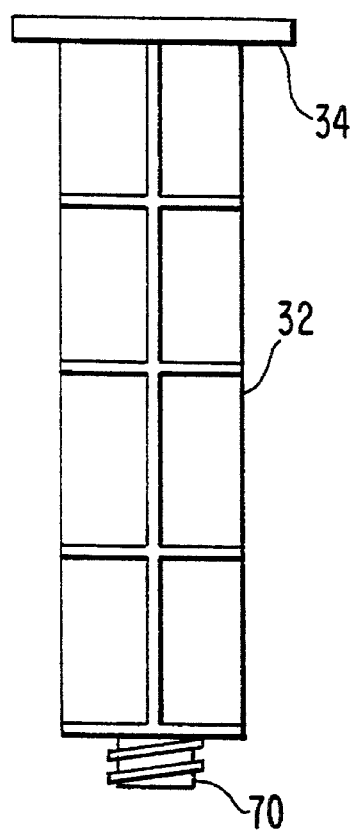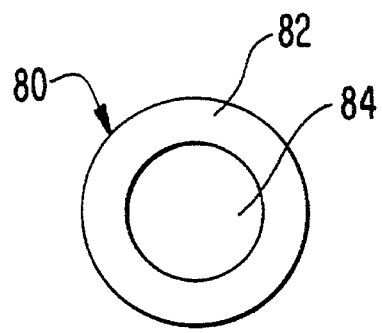

INSERT DEVICE FOR FACILITATING LIMITED ASPIRATION OF A DELIVERY APPARATUS

This application is a division of Ser. No. 988,275, filed Dec. 14, 1992, now U.S. Pat. No. 5,370,621.

FIELD OF THE INVENTION

The present invention relates to delivery apparatus such as syringe assemblies that include a container portion in which a piston is slidably movable to expel fluid material disposed in the container portion. Specifically, the invention relates to such syringes in which the movement of the piston is restricted or limited.

DESCRIPTION OF THE PRIOR ART

Delivery apparatus in the form of syringes having a hollow cylindrical barrel portion with a delivery or nozzle end and an opposite open end that receives a piston or plunger are known in the prior art. In such devices, the piston is slidable in sealing engagement within the interior surface of the barrel and is movable towards the delivery end for expelling the syringe contents. The piston can also be withdrawn to perform various tasks, e.g. aspirating fluids for disposal or for subsequent injection into a living subject, a catheter, etc.

It is further known in the art to manufacture prefilled, sterile delivery apparatus in the form of syringes that are first filled with a medical fluid, sealed to enclose the fluid within a storage volume formed by the syringe barrel, and then sterilized to provide sterile syringe assemblies with sterile contents. For a disclosure of such prefilled syringes, see e.g. U.S. Pat. Nos. 4,628,969 and 4,718,463. Prefilled, sterile syringes of the type disclosed in the referenced patents are provided to hospitals or the like in a filled, sealed and sterile condition. To use the syringes, it is only necessary to break the seal of the delivery tip or nozzle, engage the piston with appropriate driving means and dispense the sterile fluid.

In using syringes of the above-described prefilled, sterile type, the interior of the syringe barrel which forms the storage volume and the fluid contents therein are sterile, but the exterior of the syringe, including the exposed portion of the interior of the barrel disposed behind the piston, are possibly not sterile since they are exposed to ambient conditions. It is thus important that the piston not be withdrawn or retracted, since withdrawal would cause contact between the sterile contents in the storage volume and the exposed area of the barrel behind the piston. Consequently, withdrawal of the piston away from the delivery end of the barrel creates a significant contamination risk. It is, however, often desirable in a clinical situation to aspirate the syringe by withdrawing the piston a predetermined amount after connecting the piston driving means, e.g. a push rod, to the piston. But, such aspiration brings about the aforementioned contamination risks for the reasons mentioned above.

Accordingly, it is an object of the present invention to provide a delivery apparatus in which the aforementioned problems are overcome.

SUMMARY OF THE INVENTION

The present invention provides a delivery apparatus in the form of a prefilled, sterile syringe including a container portion with a piston configured to slidably engage the interior surface of the container portion in a sealing fashion, the apparatus being provided with an insert lock for allowing withdrawal of the piston away from the delivery end of the container a predetermined distance to aspirate the syringe without risking contamination of the sterile fluid contents disposed within the container portion.

Other features of the present invention will be apparent from the following description of the preferred embodiments taken in conjunction with the accompanying drawings wherein:

BRIEF DESCRIPTION OF THE DRAWINGS

FIG. 1 is a sectional view of a delivery apparatus according to a first embodiment of the present invention.

FIG. 2 is a top view of a stop member used in the embodiment of FIG. 1.

FIG. 3 is a push rod used in the embodiment of FIG. 1.

DETAILED DESCRIPTION OF THE PREFERRED EMBODIMENTS

Figure 4:
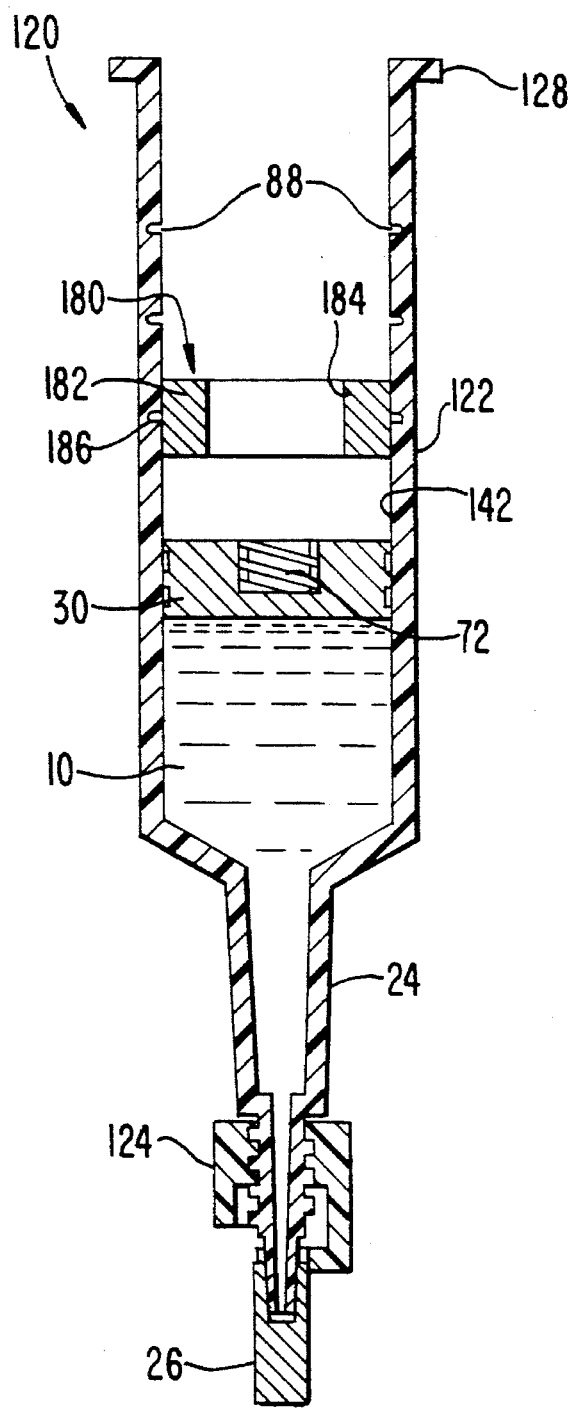
FIG. 4 is a sectional view of a delivery apparatus according to a second embodiment of the present invention.

Referring to the embodiment of the present invention shown in FIG. 1, a delivery apparatus indicated generally at 20 in the form of a syringe assembly including a container or housing portion 22 has a delivery end 24 and an opposite open end 28. A piston 30 is slidably engaged with the interior surface of container portion 22 and the delivery end 24 is sealed by a tip seal 26. The piston 30 and the delivery end 24 define a storage volume within the container portion 22 containing the fluid contents 10. As used herein, fluid means a gas, liquid, or combinations thereof. In a preferred embodiment, the fluid is a medical fluid containing a pharmaceutical media. The aforementioned storage volume is thus sealed at one end by the tip seal 26 and at the other end by the piston 30 with the fluid 10 disposed therebetween. The delivery end 24 may have means for attaching the delivery apparatus 20 to additional medical apparatus such as but not limited to threading for attaching a nut member 124 for securement to the luer connector of a conventional catheter (not shown). The syringe assembly also includes a piston rod 32 for driving the piston 30 and a stop member 80, as will be discussed below.

In a preferred embodiment of the present invention, the syringe assembly 20 is a prefilled, sterile delivery apparatus which has been presterilized to provide a sterile syringe with sterile contents. Such prefilled, sterile syringes are similar to those disclosed in U.S. Pat. Nos. 4,628,969 and 4,718,463, assigned to the same assignee as the present application, the subject matter of which patents is incorporated herein by reference. Suitable materials for fabricating the various parts of the prefilled, sterile syringe assemblies are disclosed in the aforementioned patents and can be utilized in the delivery apparatus of the present invention. These prefilled, sterile syringes are assembled, filled, sealed and sterilized to provide a sterile delivery device with sterile contents that can be shipped to hospitals or the like where they can be easily used to inject the fluid during medical diagnostic and/or treatment procedures. Since different procedures, as well as different patients, require various amounts of the fluid injectate, it is desirable to provide such prefilled syringes in various sizes or volumes, i.e. having different amounts of the fluid contents. It is further desirable from an economic standpoint to utilize a standard size syringe container portion which can be filled to various levels and then sealed to provide differing volumes of fluid, as opposed to keeping many differently sized syringe container portions on hand at the manufacturing site.

As a result, these prefilled, sterile syringes are often provided for end use in a partially filled condition, i.e. with the piston 30 disposed in the container portion 22 so as to be displaced from the open end 28, as shown in FIG. 1. As stated above, while the fluid contents 10 contained within the container portion 22 between the piston 30 and the sealed delivery end 24 are sterile, the exposed portion 42 of the interior of the container portion 22 disposed behind the piston 30 will possibly not be sterile. It is thus important that the piston 30 not be withdrawn so as to cause the sterile contents 10 to communicate with the aforementioned exposed portion 42 of the container portion 22. The use of the term "housing portion" or "barrel" will be understood to include housing portions of various shapes, and while a cylindrical housing portion is shown, non-cylindrical housing portions, such as triangular or square are encompassed by the present invention.

One solution to this problem is the prevention of piston withdrawal. This solution is suitable in situations not requiring aspiration of the syringe prior to use. However, in some clinical situations it is desirable to withdraw the piston to initially aspirate the syringe.

Pursuant to the present invention, a delivery device is provided in the form of a syringe assembly in which the piston can be withdrawn a distance of one piston thickness without contaminating the sterile syringe contents disposed in front of the piston. The reason that withdrawal of the piston one piston thickness will not contaminate the sterile contents of the syringe is that this one piston thickness portion of the container portion interior is sterile when the syringe assembly is shipped from the manufacturer. Specifically, this one piston thickness portion of the container portion interior, which contacts the fluid upon such limited withdrawal of the piston, is sterile because it is engaged by the peripheral side edge of the piston, i.e. it is not exposed to ambient conditions. Thus, contact by the sterile fluid contents with this portion of the container portion interior does not pose a risk of contamination of the fluid contents. However, any aspiration without limitations on the withdrawal of the piston in this manner creates a significant risk of contaminating the sterile fluid contents stored in the syringe container portion.

Referring to FIGS. 1–3, the first embodiment of the present invention includes the above-described partially filled syringe assembly 20 with a piston 30 having a thickness "t" disposed within container portion 22. Positioned within container portion 22 between the piston 30 and open end 28 is a stop member 80 in the form of a disk 82 with a central aperture 84. The stop member 80 is placed through the open end 28 of the container portion 22 after the syringe 20 has been filled, sealed and sterilized. The stop member 80 can alternatively be positioned in the container portion 22 after the piston 30 has been assembled to seal contents 10 therein, but before the syringe 20 has been sterilized. This is possible due to the space between piston 30 and stop member 80 which allows expansion of the fluid contents and/or piston 30 during sterilization, e.g. autoclaving. Stop member 80 can be secured in position within container portion 22 by any suitable means including but not limited to adhesive. Any suitable insertion means can be utilized to measure the appropriate distance into container portion 22 that stop member 80 should be inserted, which distance will depend on the volume of fluid 10 in container portion 22. For example, the container portion 22, which is generally transparent or translucent, can carry marking means for indicating the proper position of stop member 80 relative to a given volume of fluid contents 10, and the stop member 80, carrying adhesive on its outer periphery, can be inserted an appropriate distance into container portion 22 and secured thereto.

The stop member 80 is positioned in container portion 22 a predetermined distance "d" behind piston 30, i.e. between the piston 30 and the end 28 of syringe 20. This distance "d" is equal to the thickness "t" of piston 30 so that piston 30 can be moved in a reverse direction a distance of one piston thickness but no further. The push rod 32 shown in FIG. 3 includes a threaded protuberance 70 for engaging a complementarily threaded recess 72 in piston 30. Push rod 32 is sized so as to be insertable through aperture 84 of stop member 80 to enable attachment of push rod 32 to piston 30. After such attachment, push rod 32 is operable to move piston 30 within container portion 22, with reverse movement of push rod 32 and piston 30 permitted to the extent of one piston thickness "d". Reverse movement of piston 30 more than the distance "d" is prevented by stop member 80, which contacts the upper surface 31 of piston 30 to limit further withdrawal. Accordingly, the aforementioned contamination risks are avoided since the sterile contents 10 do not come in contact with exposed portion 42 of container portion 22.

Figure 5:
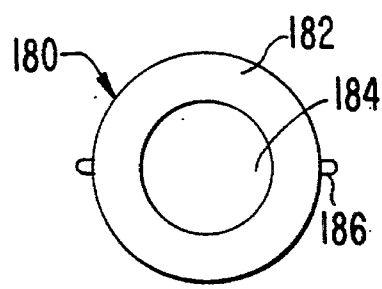
FIG. 5 is a top view of a stop member used in the embodiment of FIG. 4.
Figure 6:
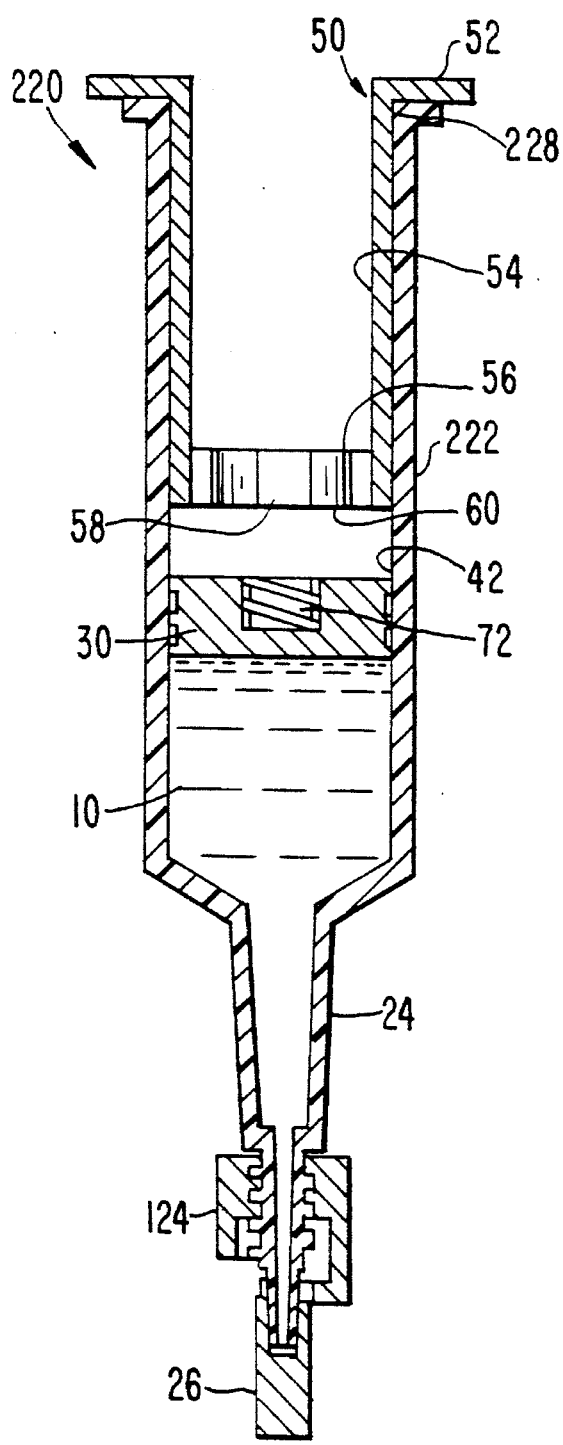
FIG. 6 is a sectional view of a delivery apparatus according to a third embodiment of the present invention.
Figure 8:
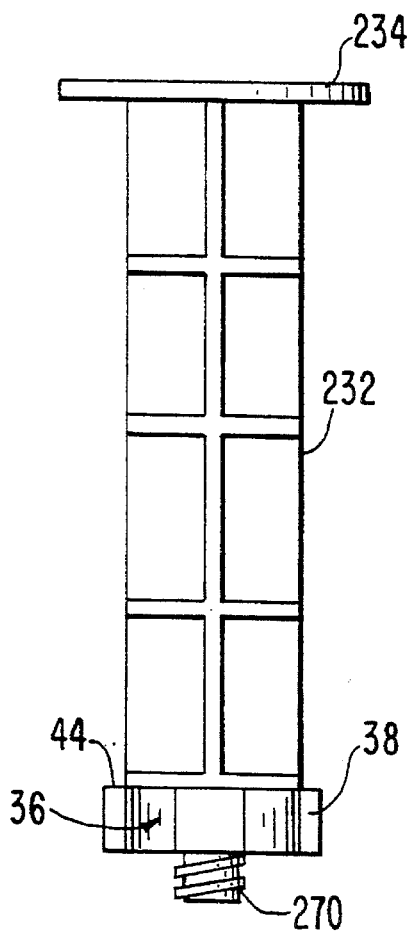
FIG. 8 is a front view of a piston rod and stop member used in the embodiment of FIG. 6.
Figure 7:
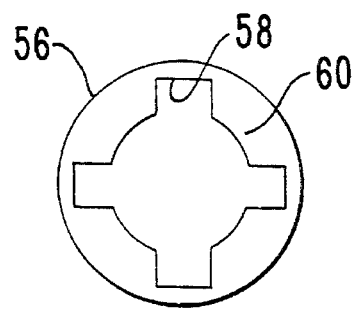
FIG. 7 is a bottom view of the insert sleeve of the embodiment shown in FIG. 6.

A second embodiment of the present invention is shown in FIGS. 4 and 5 and includes a delivery apparatus 120 in the form of a prefilled, sterile syringe assembly with a container portion 122 and a piston 30. A stop member 180 is positioned within container portion 122 behind piston 30, as in the first embodiment, a distance equal to the thickness of piston 30. The container portion 122 is provided with a series of pairs of recesses 88 disposed on the interior surface thereof for engaging a pair of lugs or protrusions 186 carried by stop member 180. The stop member 180 can be positioned within container portion 122 at different positions relative to piston 30 by selectively engaging the lugs 186 with one pair of recesses 88. The container portion 122 and stop member 180, specifically lugs 186, have sufficient inherent resiliency to allow stop member 180 to be slid into container portion 122 with lugs 186 pressed against the interior surface of container portion 122 until the lugs 186 are selectively aligned with a pair of the recesses 88. Upon such alignment, lugs 186 snap into recesses 88 to secure stop member 180 within container portion 122 the proper distance behind piston 30. The recesses 88 are shown to extend part way through the wall of container portion 122 from the interior surface thereof and are in the form of a series of pairs of depressions spaced around the container portion circumference. Optionally, the recesses 88 can be in the form of a series of longitudinally spaced annular recesses extending around the container portion 122. While three recesses 88 are shown, it will be recognized that other than three can be used, with the number of recesses determined by the different desired positions of stop member 180 corresponding to different prefilled fluid volumes of the syringe 120.

A third embodiment of the present invention is shown in FIGS. 6–11 in the form of a delivery apparatus 220 and includes a lock sleeve 50 having a flange 52 which seats on the rear flange 51 of the syringe container portion 222 and a tubular portion 54 which fits snugly within and against the interior surface of the container portion 222. The lock sleeve is positioned and secured in container portion 222 by any suitable means, including but not limited to adhesive or a tight friction fit. Additionally, the flange 52 of lock sleeve 50 is optional in that a sleeve 50 without flange 52 (not shown) can be secured in container portion 222 with the upper end of the sleeve 50 flush with the upper end 28 of the container portion 222. The lock sleeve 50 further includes an apertured disk portion 56 positioned at the lower end of tubular portion 54, this disk portion containing a plurality of notches or openings 58 as best seen in FIG. 2. While the embodiment shown has four notches 58, those skilled in the art will recognize that it is possible to utilize more or less than four such openings. The notches 58 are configured in size and shape to receive stop pins 38 which extend radially outward from a stop member 36 disposed at the lower end of piston rod 232, as shown in FIGS. 3 and 4. The lock sleeve 50 may be comprised of separate members, i.e. tubular portion 54 and disk 56 may be secured together and to syringe container portion 222 by suitable means, or alternatively may be formed integrally with syringe container portion 222.

The lock sleeve 50 fits within the container portion 222 so as to be spaced above the piston 30 a predetermined distance for reasons discussed above. The stop member 36, which can be formed integrally with the piston rod 232, or alternatively can be a separate member secured thereto, is adapted to be inserted through the lock sleeve 50 so that an attachment means 70 contacts piston 30, thereby securing the piston rod 232 to the piston 30. A non-limiting example of such attachment means is a threaded protuberance 70 extending downward from stop member 36 which protuberance can be rotated into engagement with a threaded recess 72 formed in piston 30. Placement of the piston rod 32 and stop member 36 through the lock sleeve 50 is accomplished by positioning the piston rod 232 such that the stop pins 38 are aligned with the notches 58 formed in the lock sleeve 50, and then simply moving the piston rod 232 towards the delivery end 24 whereby attachment means 70 engages the piston 30. The piston rod 232 is attached or rotated into connection with the piston 30 so that the stop pins 38 are not in alignment with the notches 58 of the lock sleeve 50, best seen in FIG. 11. This facilitates aspiration without contamination of fluid 10, as discussed below. With the piston rod 232 thus secured to the piston 30, it is now possible to perform initial aspiration without the aforementioned risk of contaminating the sterile fluid 10.

Figure 10:
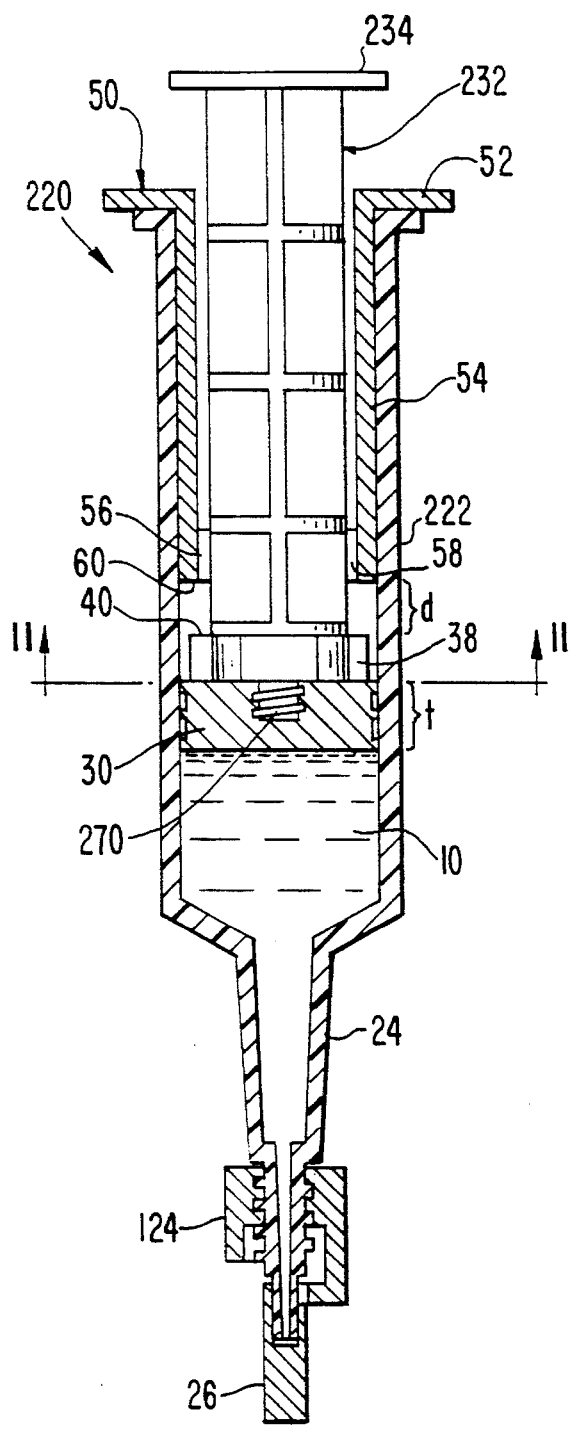
FIG. 10 is a sectional view of the delivery apparatus according to the third embodiment of the present invention in assembled and ready to use condition.
Figure 9:
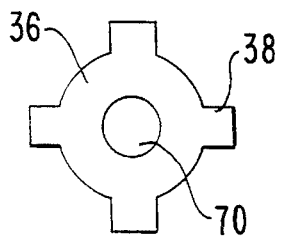
FIG. 9 is a bottom view of the piston rod and stop member shown in FIG. 6.
Figure 11:
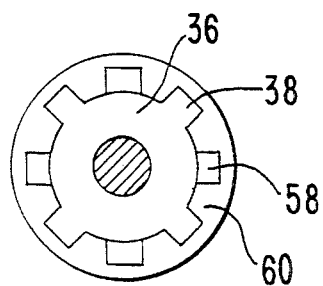
FIG. 11 is a sectional view of the piston rod and lock sleeve taken along lines 11—11 of FIG. 10.

As shown in FIG. 10, the piston rod 232 is secured to the piston 30 with the lower surface of the stop member 36 abutting the upper surface of the piston 30. The upper surface 40 of stop member 36 is spaced below the lower surface 60 of disk portion 56 of the lock sleeve 50 a distance "d", which distance "d" is the thickness of piston 30. Consequently, withdrawal of the piston rod 232 is possible only to the extent of the distance "d" since the upper surface 40 of stop member 36 abuts the lower surface 60 of disk portion 56 upon such withdrawal. This abutment occurs because the stop pins 38 are not aligned with the notches 58, as shown in FIG. 11, thus the stop member 36 cannot be moved past the disk portion 56 of lock sleeve 50. Limited aspiration of the apparatus by withdrawing the piston 30 a distance "d" is now possible without risk of contamination of the sterile fluid 10.

While the present invention and the embodiments presented herein have been set forth and described in detail for the purposes of making a full and complete disclosure of the subject matter thereof, the disclosure herein presented is not intended to be limiting in any way with respect to the true scope of this invention as the same is set forth in the appended.

What is claimed is:

1. A delivery apparatus comprising:

a container portion having a delivery end, an opposite open end adapted to receive a piston, and a plurality of recesses formed along an interior surface of said container portion;

a piston having a predetermined thickness, said piston adapted to be positioned in said container portion so as to be slidable in sealing engagement against an interior surface of said container portion;

means connected to said piston for moving said piston within said container portion along said interior surface in a direction toward said delivery end to expel material contained within said container portion; and means for permitting movement of the piston in a direction away from said delivery end a distance substantially equal to said piston thickness, but preventing movement of the piston in said direction away from said delivery end more than said distance;

wherein said means for permitting movement is a separate insert member positionable in said container portion through said open end of said container portion;

said insert member being selected from the group consisting of a sleeve with a bottom disc portion adapted to overlie the piston, and a stop member selectively positionable at a desired location in said container portion;

wherein said stop member includes at least one protrusion configured to selectively engage one of said plurality of recesses formed along said interior surface of said container portion.

2. A delivery apparatus as claimed in claim 1, wherein said means for moving the piston towards said delivery end includes a push rod connected to said piston.

3. A delivery apparatus as claimed in claim 1, wherein said insert member is configured for placement in said container portion so as to spaced above the piston a distance of substantially one piston thickness, whereby upon withdrawal of the piston said insert member limits withdrawal to said distance.

4. A delivery apparatus as claimed in claim 3, wherein said means for moving the piston towards said delivery end includes a piston rod for connection to said piston, the piston rod having at least one stop pin extending therefrom.

5. A delivery apparatus as claimed in claim 4, wherein said insert member has at least one opening formed therein for receiving said at least one stop pin so that the piston rod can be placed through the insert member, into the container portion and connected to the piston.

6. A delivery apparatus as claimed in claim 5, wherein said insert member is in the form of a sleeve with a bottom disk portion adapted to overlie the piston, said at least one opening being formed in the disk portion, and said disk portion adapted to abut said at least one stop pin to limit withdrawal of the piston rod and piston.

7. A delivery apparatus comprising:

a container portion having a delivery end and an opposite open end adapted to receive a piston;

a piston having a predetermined thickness, said piston adapted to be positioned in said container portion so as to be slidable in sealing engagement against an interior surface of said container portion;

said container portion being selected from the group consisting of a container portion having a substantially smooth interior surface, and a container portion having a plurality of circumferential recesses therein for engagement with a corresponding protrusion of a piston stop member;

means connected to said piston for moving said piston within said container portion along said interior surface in a forward direction toward said delivery end to expel material contained within said container portion; and a stop member permitting movement of the piston in a reverse direction away from said delivery end a distance substantially equal to said piston thickness, but preventing movement of the piston in said reverse direction more than said distance, wherein said stop member is an insert member positionable within said container portion through the open end thereof so as to overlie said piston, said stop member being selected from the group consisting of a sleeve with a bottom disc portion adapted to overlie the piston and a cylindrical stop member selectively positionable at different locations in said container portion, the selectively positionable cylindrical stop member including a cylindrical outer surface corresponding to and received within the interior surface of said container portion, the outer surface of said cylindrical stop member including at least one protrusion extending outwardly therefrom and configured to selectively engage one of said plurality of circumferential recesses in said container portion.

8. A delivery apparatus comprising:

a container portion having a delivery end and an opposite open end adapted to receive a piston;

a piston having a predetermined thickness, said piston adapted to be positioned in said container portion so as to be slidable in sealing engagement against an interior surface of said container portion;

means connected to said piston for moving said piston within said container portion along said interior surface in a forward direction toward said delivery end to expel material contained within said container portion; and a stop member permitting movement of the piston in a reverse direction away from said delivery end a distance substantially equal to said piston thickness, but preventing movement of the piston in said reverse direction more than said distance, wherein said stop member is an insert member positionable within said container portion through the open end thereof so as to overlie said piston, wherein said insert member is a sleeve with a bottom disc portion thereof adapted to overlie said piston.

* * * * *